(12) United States Patent
Liu et al.

(10) Patent No.: US 8,808,671 B2
(45) Date of Patent: Aug. 19, 2014

(54) NON-TUMORIGENIC OINTMENT/CREAM BASE FOR TOPICAL APPLICATION

(75) Inventors: Jue-Chen Liu, New Brunswick, NJ (US); Jeff Wu, New Brunswick, NJ (US); Allan H. Conney, Princeton, NJ (US)

(73) Assignees: Rutgers, The State University of New Jersey, New Brunswick, NJ (US); Johnson & Johnson Consumer Companies, Inc., Skillman, NJ (US)

( * ) Notice: Subject to any disclaimer, the term of this patent is extended or adjusted under 35 U.S.C. 154(b) by 1324 days.

(21) Appl. No.: 12/063,603

(22) PCT Filed: Aug. 29, 2006

(86) PCT No.: PCT/US2006/033752
§ 371 (c)(1), (2), (4) Date: Aug. 11, 2008

(87) PCT Pub. No.: WO2007/027704
PCT Pub. Date: Mar. 8, 2007

(65) Prior Publication Data
US 2009/0149556 A1    Jun. 11, 2009

Related U.S. Application Data

(60) Provisional application No. 60/712,096, filed on Aug. 29, 2005.

(51) Int. Cl.
*A61K 8/00* (2006.01)
*A61K 8/18* (2006.01)
*A61Q 17/04* (2006.01)
*A61K 8/02* (2006.01)

(52) U.S. Cl.
USPC ............................................ 424/59; 424/401

(58) Field of Classification Search
USPC ...................................................... 424/59, 401
See application file for complete search history.

(56) References Cited

U.S. PATENT DOCUMENTS

| 5,000,937 | A | * | 3/1991 | Grollier et al. | 424/47 |
| 5,015,471 | A | * | 5/1991 | Birtwistle et al. | 424/70.19 |
| 5,762,947 | A | * | 6/1998 | Guerrero et al. | 424/401 |
| 6,506,375 | B1 | * | 1/2003 | Barr | 424/74 |
| 7,858,607 | B2 | * | 12/2010 | Mamchur | 514/177 |

FOREIGN PATENT DOCUMENTS

EP    1348441    1/2003

* cited by examiner

*Primary Examiner* — Mina Haghighatian
*Assistant Examiner* — Luke Karpinski
(74) *Attorney, Agent, or Firm* — Robert C. Netter, Jr.; Dann, Dorfman, Herrell & Skillman, P.C.

(57) ABSTRACT

A non-tumorigenic skin care composition is provided.

4 Claims, 4 Drawing Sheets

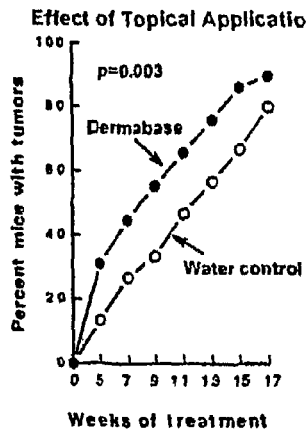
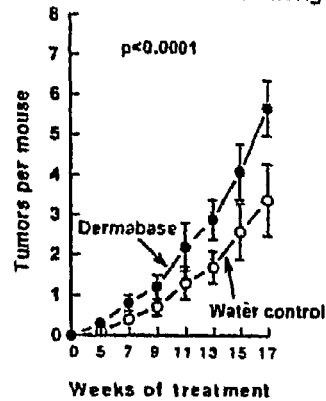
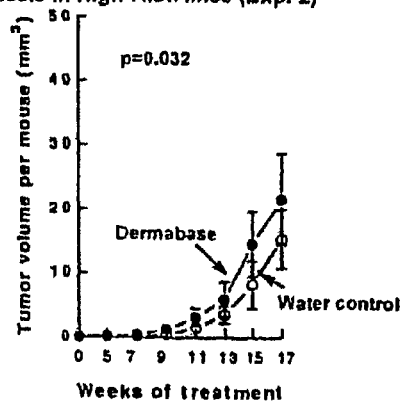
Fig. 3A Fig. 3B Fig. 3C
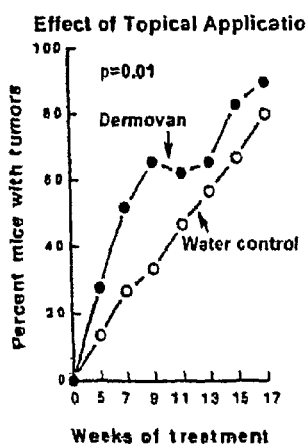
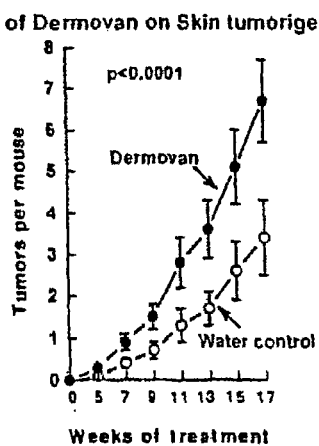
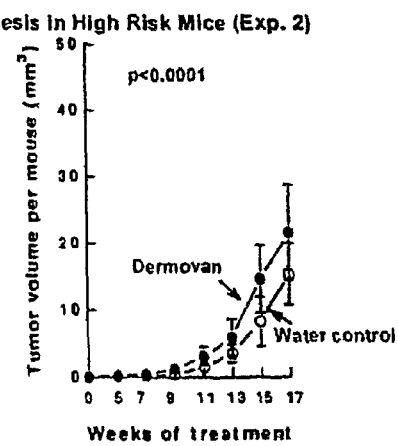
Fig. 4A Fig. 4B Fig. 4C

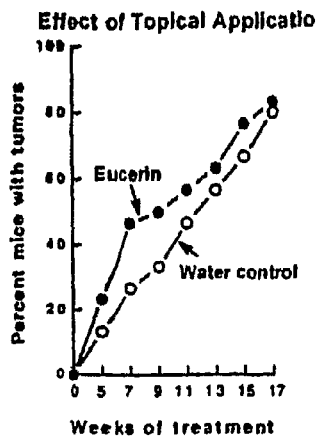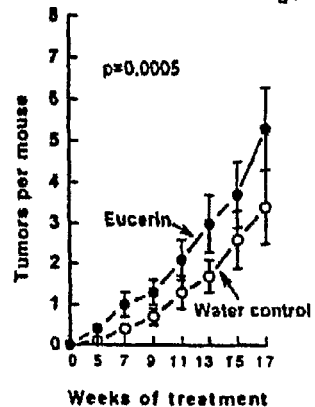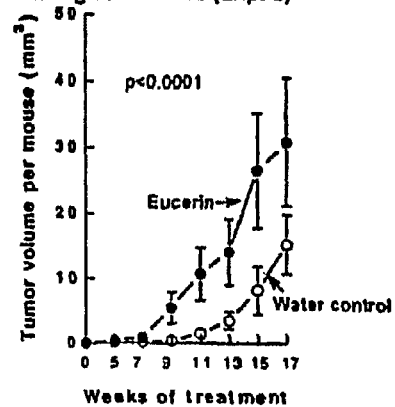
Fig. 5A  Fig. 5B  Fig. 5C
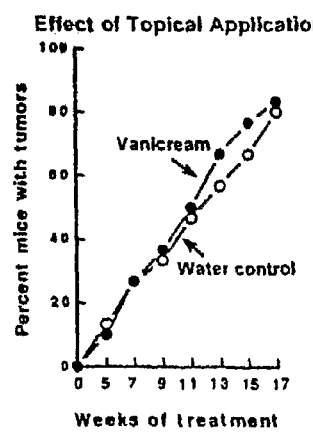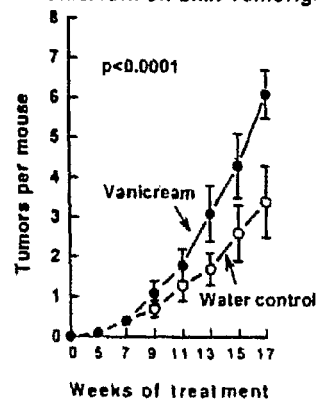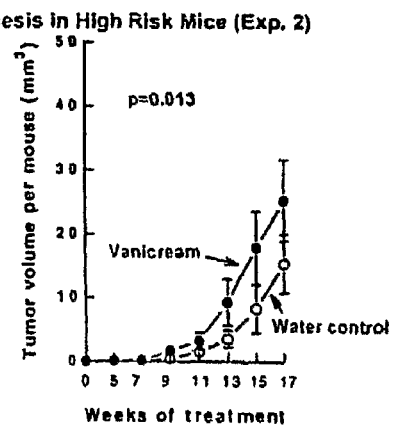
Fig. 6A  Fig. 6B  Fig. 6C

NON-TUMORIGENIC OINTMENT/CREAM BASE FOR TOPICAL APPLICATION

This application is a §371 application of PCT/US2006/033752, filed Aug. 29, 2006, which in turn claims priority under 35 U.S.C. §119(e) to U.S. Provisional Application 60/712,096 filed Aug. 29, 2005. The entire disclosure of each of the foregoing applications is incorporated herein by reference as though set forth in full.

Pursuant to 35 U.S.C. §202 (c), it is acknowledged that the U.S. Government has certain rights in the invention described herein, which was made in part with funds from the National Institutes of Health, Grant Numbers NIH CA80759 and PHS CA88961.

FIELD OF THE INVENTION

The present invention relates to skin care compositions. More specifically, the invention relates to improved ointment or cream bases which exhibit reduced tumorigenic properties relative to other conventionally employed ointment/cream formulations.

BACKGROUND OF THE INVENTION

Several publications and patent documents are cited throughout the specification in order to describe the state of the art to which this invention pertains. Each of these citations is incorporated herein by reference as though set forth in full.

Consumers have long desired a moisturizing and conditioning preparation in the form of a hand and body lotion or cream which, when applied, provides cosmetically acceptable tactile properties. Furthermore, because of the wide variety of skin, hair and nail problems faced by consumers, personal care products which can deliver and/or deposit benefit materials that alleviate such problems are highly desirable.

Clearly, any such cream or lotion should be non-toxic and safe for repeated application. Surprisingly, the present inventors have discovered that certain of the commercially available creams and lotions are not ideal for repeated application. It is therefore an object of the present invention to provide a superior, non-toxic ointment for use in formulations suitable for delivering beneficial therapeutic agents to the skin of a test subject.

SUMMARY OF THE INVENTION

In accordance with the present invention, a composition which lacks tumorigenicity (also referred to herein as "custom blend") is provided, comprising purified water, propylene glycol, stearyl alcohol, cetyl alcohol, polysorbate 20, isopropyl myristate, C12-15 alkyl benzoate, benzoic acid, glycerin, and sodium hydroxide (pH 5.8).

The topical compositions of the present invention may be used for a variety of uses, including, but not limited to, treating, cleansing, beautifying, or covering the skin or hair of a human. The compositions, thus, may be made into a wide variety of product types. These include, but are not limited to lotions, powders, masks, creams, gels, milky lotions, sticks, sprays, ointments, pastes, mousses, shampoos, cosmetics, and dermal patches. Products include, but are not limited to, lip balms, moisturizing and sunscreen lotions/creams, skin cleansing compositions (e.g., facial scrubs), and body mists.

In yet another embodiment, the compositions of the invention may further comprise a therapeutic agent. Such agents include, without limitation, sunscreens, anti-aging agents, chemotherapeutic agents, chemopreventative agents, steroids, anti-inflammatory agents, pigment modulating agents, exfoliating agents, wound-healing agents, anti-irritation agents, anti-cellulite agents, anti-fungal agents, anti-bacterial agents, moisturizing agents, emollients and anti-viral agents.

The composition may also comprise a nutrient, such as vitamins, essential amino acids, and essential fatty acids. Exemplary vitamins include, without limitation, Vitamin A, Vitamin B, Vitamin C, and Vitamin E.

BRIEF DESCRIPTION OF THE DRAWINGS

FIGS. 3A-3C are a series of graphs showing the tumorigenic effects of topical administration of Dermabase in a repeat of the experiment shown in FIG. 1 (Exp. 2; note: this experiment included the use of topical water as a control).

FIGS. 4A-4C are a series of graphs showing the tumorigenic effects of topical administration of Dermovan on high risk mice (Exp. 2).

FIGS. 5A-5C are a series of graphs showing the tumorigenic effects of topical administration of Eucerin on high risk mice (Exp. 2).

FIGS. 6A-6C are a series of graphs showing the tumorigenic effects of topical administration of Vanicream on high risk mice (Exp. 2).

DETAILED DESCRIPTION OF THE INVENTION

Figures 1A, 1B, 1C:
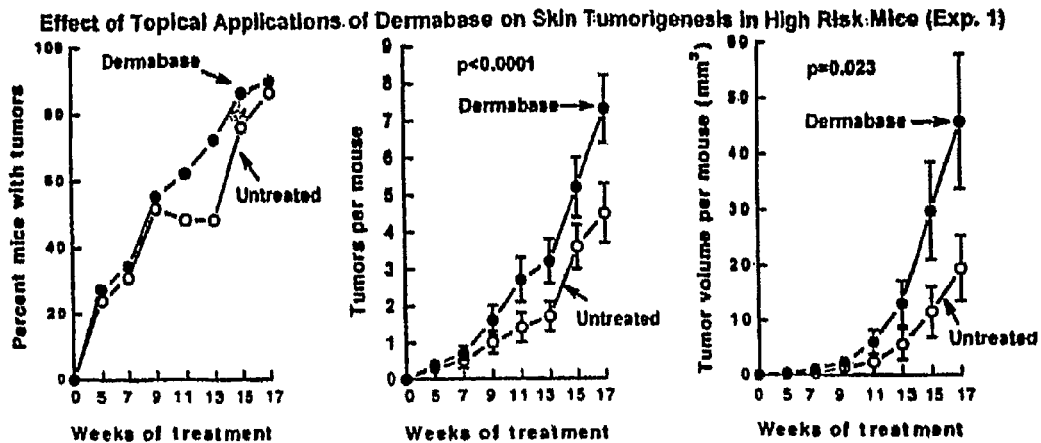
FIGS. 1A-1C are a series of graphs showing the tumorigenic effects of topical administration of Dermabase on high risk mice (Exp. 1).
Figures 2A, 2B, 2C:
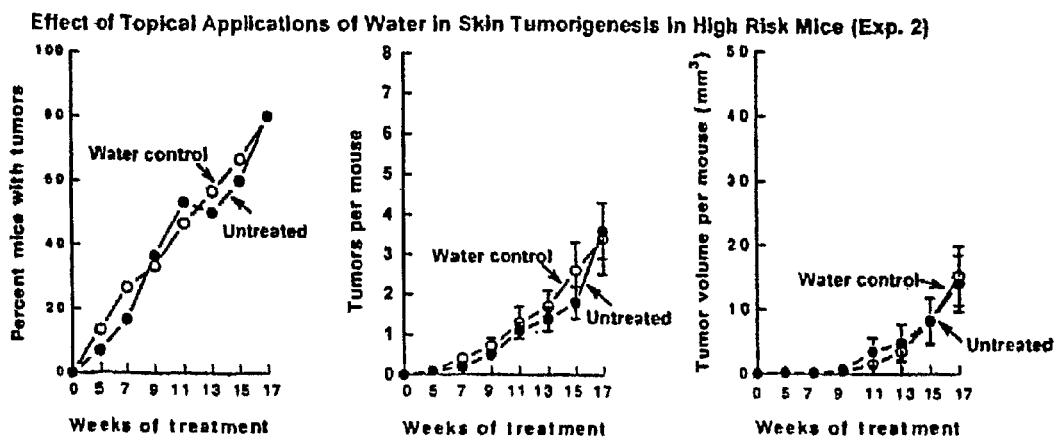
FIGS. 2A-2C are a series of graphs showing the tumorigenic effects of topical administration of water on high risk mice (Exp. 2).
Figure 7A:
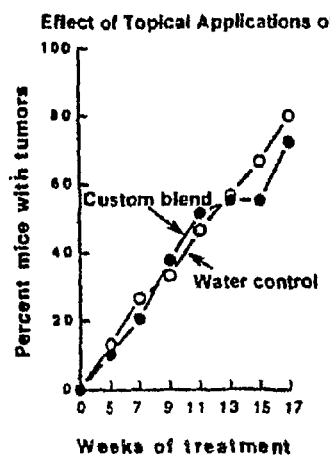
FIGS. 7A-7C are a series of graphs showing the tumorigenic effects of topical administration of the composition of the invention on high risk mice (Exp. 2).
Figure 7B:
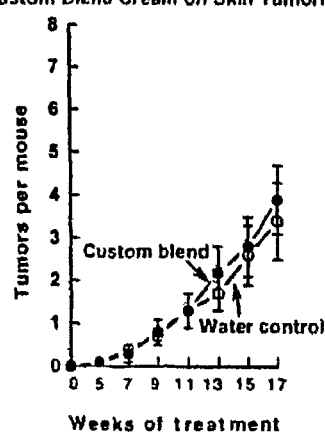
Figure 7C:
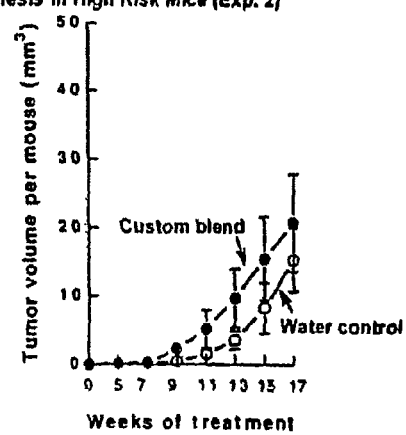

The ingredients of Dermabase, (purified water, mineral oil, petrolatum, cetostearyl alcohol, propylene glycol, sodium laurel sulfate, isopropyl palmitate, imidazolidinyl urea, methylparaben and propylparaben) are substances that are believed to be safe and are used in many dermatological preparations. Additionally, the ingredients in other creams, such as Dermovan, Eucerin, and Vanicream were also considered safe for repeated topical use. One goal of our present research is to formulate new ointment based therapeutic and preventative agents. Before creating these formulations we wanted to ensure that the use of conventional creams, such as Dermabase, as a carrier vehicle was clinically safe. The data presented below indicate that many conventionally used ointments and creams are not suitable for delivery of therapeutically beneficial agents See FIGS. 1-7 and Tables 1 and 2. Accordingly, a safer ointment vehicle has been developed.

The following materials and methods are provided to facilitate the practice of the present invention.

Determination of Tumorigenicity:

Female SKH-1 hairless mice were treated with UVB (30 mJ/cm$^2$) twice a week for 20 weeks to obtain tumor free "high risk" mice. The mice were then untreated, treated topically with water (100 µl) or with the indicated ointment/cream (100 mg) once a day, 5 days a week for 17 weeks in the absence of further treatment with UVB. The data in FIGS. 1-7 are expressed as the mean±S.E. Statistical analyses of differences in pair-wise regression slopes of rates of change with time were determined for tumors per mouse and for tumors volume per mouse and are indicated. The statistical analysis of percent mice with tumors was based on a comparison of tumor free distribution between the two groups by the log rank test. The lack of a p-value for the comparison of the curves in FIG. 7 indicates a lack of statistical significance (p>0.05).

The following examples are provided to illustrate certain embodiments of the invention. They are not intended to limit the invention in any way.

EXAMPLE I

The composition of the invention is prepared as follows:

Water, propylene glycol and glycerin are added to a beaker according to the formula proportions. The contents are then heated to 75-80° C. with mixing. Polysorbate 20, cetyl alcohol, stearyl alcohol, isopropyl myristate, stearyl alcohol, C12-15 alkyl benzoate and benzoic acid at the indicated proportions are then added into a second beaker and mixed with heating at 75° C. The contents of the second beaker are then added to the first beaker and the contents heated for an additional 10 minutes at 75° C. with stirring. The mixture is cooled to approximately 30° C. and the pH adjusted to 5.9 using 20% NaOH.

The components of the skin care composition may be present in the formulation in the following ranges.

|  | % (wt/wt) |
|---|---|
| Water | 55-70 |
| Glycerin | 0.02-20 |
| Propylene glycol | 0.1-30 |
| Stearyl alcohol | 3-15 |
| Cetyl alcohol | 0.1-15 |
| Polysorbate 20 | 0.1-5 |
| Isopropyl myristate | 0.01-3 |
| C12-C15 Alkyl benzoate | 0.01-5 |
| Benzoic acid | 0.01-1 |

A suitable pH is between 4 and 8, with 5-7 being preferred.

A preferred non-tumorigenic topical composition in accordance with the invention has the following formulation:

|  | % (wt/wt) |
|---|---|
| Water | 64.90 |
| Propylene Glycol | 20.0 |
| Glycerin | 0.20 |
| Stearyl Alcohol | 8.50 |
| Cetyl Alcohol | 3.00 |
| Polysorbate 20 | 2.00 |
| Isopropyl Myristate | 1.00 |
| C12-15 Alkyl Benzoate | 0.20 |
| Benzoic Acid | 0.20 |
| Total | 100.00 |

EXAMPLE 2

In our initial study (Experiment 1), Dermabase was tested for tumorigenic activity in UVB pretreated "high risk" mice prior to doing extensive studies using Dermabase as a delivery vehicle for therapeutic agents in humans. In a preliminary study, we treated SKH-1 hairless mice with UVB (30 mJ/cm2) twice a week for 20 weeks to obtain "high risk" mice without tumors but with a high risk of developing skin tumors during the subsequent 20 weeks. One group of these "high risk" mice was treated for 18 weeks with approximately 100 mg of the indicated ointment or cream topically once a day, 5 days a week, in the absence of further treatment with UVB, and the control group was untreated. In this study and in subsequent studies with the ointment/cream bases, we used a Q-tip to gently rub the ointments or creams into the dorsal epidermis. The results of gross tumor counts during the course of the study indicated that Dermabase had tumorigenic activity in UVB-pretreated mice (See FIG. 1A-C and FIG. 3 A-C) and careful histological examination of the epidermis of these mice indicated that treatment of the "high risk" mice with Dermabase for 18 weeks caused an increase in (a) the percentage of mice with squamous cell carcinomas, (b) the number of keratoacanthomas and squamous cell carcinomas per mouse and (c) the size of squamous cell carcinomas per mouse, when compared with untreated mice. See Tables 1 and 2. These results indicate that Dermabase is unsuitable for use as a delivery vehicle in humans, particularly in patients at risk for developing cancer. Thus, a new topical composition in accordance with the invention has been developed which does not promote tumorigenesis in high risk mice previously exposed to UVB.

In a second carcinogenesis experiment (Exp. 2), UVB-pretreated "high risk" mice were treated topically with approximately 100 mg of Dermabase (i.e., repeating experiment 1), Dermovan, Eucerin Original Moisturizing Cream (Eucerin), Vanicream, and the specially formulated composition of the invention. Each of the foregoing was applied once a day, 5 days a week. In this study, we have two control groups—one group is untreated and the other group is treated topically with approximately 100 μL of water once a day 5 days a week to control for the stress of removal of the mice from their cages and gently rubbing their backs with a Q-tip as was done with the various ointment bases.

TABLE 1

Stimulatory effect of topical applications of Dermabase cream on the formation of skin tumors in high risk SKH-1 mice previously treated with ultraviolet B light

| Treatment | No. of mice | Squamous cell papillomas | | Keratoacanthomas | | Total nonmalignant tumors | | Squamous cell carcinomas | | Total tumors | |
|---|---|---|---|---|---|---|---|---|---|---|---|
| | | Percent of mice with tumors | Tumors per mouse | Percent of mice with tumors | Tumors per mouse | Percent of mice with tumors | Tumors per mouse | Percent of mice with tumors | Tumors per mouse | Percent of mice with tumors | Tumors per mouse |
| Untreated | 29 | 10 | 0.10 ± 0.06 | 86 | 6.41 ± 1.16 | 86 | 6.52 ± 1.19 | 24 | 0.41 ± 0.15 | 86 | 6.93 ± 1.28 |
| Dermabase | 28 | 7 | 0.11 ± 0.08 | 96 | 11.36 ± 1.37$^a$ (77) | 96 | 11.46 ± 1.39$^a$ (76) | 50$^b$ (108) | 0.93 ± 0.22$^b$ (127) | 96 | 12.39 ± 1.53$^a$ (79) |

Female SKH-1 mice (7-8 weeks old) were irradiated with UVB (30 mJ/cm$^2$) twice weekly for 20 weeks, and UVB irradiation was stopped. These tumor-free mice with a high risk of developing skin tumors were untreated or treated topically with 100 mg of Dermabase cream once a day five days a week for 17 weeks. The mice were sacrificed at 18 weeks after the last dose of UVB, and all tumors were characterized by histopathology studies. Each value is the mean ± SE, and the numbers in parentheses represent percent increase.
Statistically different from the untreated control group ($^a$p < 0.0001, $^b$p = 0.021). Details of the statistical analyses are given in Appendix C.

TABLE 2

Effect of topical applications of Dermabase cream on the size of tumors in high risk SKH-1 mice previously treated with ultraviolet B light

| Treatment | No. of mice | Squamous cell papillomas | | Keratoacanthomas | | Total nonmalignant tumors | | Squamous cell carcinomas | | Total tumors | |
|---|---|---|---|---|---|---|---|---|---|---|---|
| | | Tumor volume per tumor (mm³) | Tumor volume per mouse (mm³) | Tumor volume per tumor (mm³) | Tumor volume per mouse (mm³) | Tumor volume per tumor (mm³) | Tumor volume per mouse (mm³) | Tumor volume per tumor (mm³) | Tumor volume per mouse (mm³) | Tumor volume per tumor (mm³) | Tumor volume per mouse (mm³) |
| Untreated | 29 | 20.0 ± 16.7 | 2.1 ± 1.8 | 4.7 ± 1.0 | 29.9 ± 9.5 | 4.9 ± 1.0 | 32.0 ± 9.9 | 45.5 ± 10.2 | 18.8 ± 8.1 | 7.3 ± 1.3 | 50.8 ± 14.7 |
| Dermabase | 28 | 28.8 ± 25.3 | 3.1 ± 2.8 | 4.3 ± 0.6 | 48.9 ± 10.6$^c$ (64) | 4.5 ± 0.6 | 52.0 ± 11.9$^d$ (63) | 73.2 ± 15.0 | 68.0 ± 24.5$^b$ (262) | 9.7 ± 1.6 | 120.0 ± 33.0$^a$ (136) |

Female SKH-1 mice (7-8 weeks old) were irradiated with UVB (30 mJ/cm²) twice weekly for 20 weeks, and UVB irratiation was stopped. These tumor-free mice with a high risk of developing skin tumors were untreated or treated topically with 100 mg of Dermabase cream once a day five days a week for 17 weeks. The mice were sacrificed at 18 weeks after the last dose of UVB, and all tumors were characterized by histopathology studies (Table 7) and the size of each tumor was determined. Each value is the mean ± SE, and the numbers in parentheses represent percent increase.
Statistically different from the untreated control group ($^a$p = 0.032, $^b$p = 0.041, $^c$p = 0.050, $^d$p = 0.062). Details of the statistical analyses are given in Appendix C.

TABLE 3

Effect of topical applications of Custom Blend cream on the formation of skin tumors in high risk SKH-1 mice previously treated with ultraviolet B light

| Treatment | No. of mice | Squamous cell papillomas | | Keratoacanthomas | | Total nonmalignant tumors | | Squamous cell carcinomas | | Total tumors | |
|---|---|---|---|---|---|---|---|---|---|---|---|
| | | Percent of mice with tumors | Tumors per mouse | Percent of mice with tumors | Tumors per mouse | Percent of mice with tumors | Tumors per mouse | Percent of mice with tumors | Tumors per mouse | Percent of mice with tumors | Tumors per mouse |
| Water | 30 | 6.7 | 0.07 ± 0.05 | 77 | 4.30 ± 1.12 | 77 | 4.37 ± 1.14 | 17 | 0.20 ± 0.09 | 77 | 4.57 ± 1.21 |
| Custom Blend | 25 | 4.0 | 0.04 ± 0.04 | 72 | 4.68 ± 1.13 | 72 | 4.72 ± 1.13 | 12 | 0.16 ± 0.09 | 72 | 4.88 ± 1.19 |

Female SKH-1 mice (7-8 weeks old) were irradiated with UVB (30 mJ/cm²) twice weekly for 20 weeks, and UVB was stopped. These tumor-free mice with a high risk of developing skin tumors were treated topically with 100 μl of water or 100 mg of Custom Blend cream once a day five days a week for 17 weeks. The mice were sacrificed at 18 weeks after the last dose of UVB, and all tumors were characterized by histopathology studies. Each value is the mean ± S.E. No statistically significant differences were observed between the two groups. Details of the statistical analyses are given in Appendix D.

TABLE 4

Effect of topical application of Custom Blend cream on the size of tumors in high risk SKH-1 mice previously treated with ultraviolet B light

| Treatment | No. of mice | Squamous cell papillomas | | Keratoacanthomas | | Total nonmalignant tumors | | Squamous cell carcinomas | | Total tumors | |
|---|---|---|---|---|---|---|---|---|---|---|---|
| | | Tumor volume per tumor (mm³) | Tumor volume per mouse (mm³) | Tumor volume per tumor (mm³) | Tumor volume per mouse (mm³) | Tumor volume per tumor (mm³) | Tumor volume per mouse (mm³) | Tumor volume per tumor (mm³) | Tumor volume per mouse (mm³) | Tumor volume per tumor (mm³) | Tumor volume per mouse (mm³) |
| Water | 30 | 9.2 ± 5.0 | 0.6 ± 0.5 | 3.5 ± 0.7 | 15.3 ± 4.2 | 3.6 ± 0.7 | 15.9 ± 4.3 | 36.8 ± 11.4 | 7.4 ± 3.5 | 5.1 ± 1.0 | 23.2 ± 6.6 |
| Custom Blend | 25 | 33.5 | 1.3 | 3.4 ± 0.8 | 16.1 ± 5.3 | 3.7 ± 0.8 | 17.4 ± 5.3 | 48.0 ± 28.4 | 7.7 ± 5.9 | 5.1 ± 1.3 | 25.1 ± 9.8 |

Female SKH-1 mice (7-8 weeks old) were irradiated with UVB (30 mJ/cm²) twice weekly for 20 weeks, and UVB was stopped. These tumor-free mice with a high risk of developing skin tumors were treated topically with 100 μl of water or 100 mg of Custom Blend ream once a day five days a week for 17 weeks. The mice were sacrificed at 18 weeks after the last dose of UVB. All tumors were characterized by histopathology studies (Table 9) and the size of each tumor was determined. Each value is the mean ± S.E. No statistically significant differences were observed between the two groups. Details of the statistical analyses are given in Appendix D.

The results of this study indicate that the untreated control group is not different from the water-treated control group and that Dermabase, Dermovan, Eucerin and Vanicream have tumorigenic activity (See FIGS. 1, 3, 4, 5 and 6). The results also show that the composition of the invention (FIG. 7) has no statistically significant tumorigenic activity (p>0.05). This finding was confirmed by histological analysis on mice treated with the composition of the invention. See Tables 3 and 4.

As mentioned above, following treatment, the mice were sacrificed at 18 weeks after the last dose of UVB, and all tumors were characterized by histopathology studies. See Tables 1-4. Several different tumor types were observed. These included squamous cell papillomas, keratocanthomas, non-malignant tumors, and squamous cell carcinomas. Treatment of the mice with Dermabase caused a statistically significant increase in the number and size of keratocanthomas and squamous cell carcinomas per mouse. See Tables 1 and 2. Treatment of the mice with the composition of the invention did not result in a statistically significant increase in the number or size of tumors. See Tables 3 and 4.

A similar experiment was performed comparing tumor formation in mice treated with water or the custom blend of the invention following irradiation as described above. Again, a variety of tumor types were observed. 77% of the irradiated mice treated with water developed tumors as compared to 72% of the mice treated with the custom blend. Tumor volume in both groups was fairly similar (23.2±6.6 vs. 25.1±9.8).

The above results clearly demonstrate that the composition of the invention lacks the capacity to induce tumor formation in high risk mice. Accordingly, the new blend provides a suitable vehicle for delivery of therapeutic agents in humans. Such agents include, without limitation, sunscreens, anti-aging agents, chemotherapeutic agents, chemopreventive agents, exfoliating agents, pigment modulating agents, anti-cellulite agents, wound-healing agents, anti-irritation agents, steroids, anti-inflammatory agents, anti-fungal agents, anti-bacterial agents, moisturizing agents, emollients and anti-viral agents.

The composition may also comprise a nutrient, such as vitamins, essential amino acids, and essential fatty acids. Exemplary vitamins include, without limitation, Vitamin A, Vitamin B, Vitamin C, and Vitamin E.

Protocols and procedures which facilitate formulation of the topical compositions of the invention can be found in Cosmetic Bench Reference 2005, Published by Cosmetics & Toiletries, Allured Publishing Corporation, Illinois, USA, 2005 and in. *International cosmetic ingredient dictionary and handbook*. 10th ed. Edited by Tatra E. Gottschalck and Gerald E. McEwen. Washington, Cosmetic, Toiletry and Fragrance Association, 2004 each of the foregoing references being incorporated herein by reference.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A non-tumorigenic topical composition consisting of water, glycerin, propylene glycol, stearyl alcohol, cetyl alcohol, polysorbate 20, isopropyl myristate, C12-15 alkyl benzoate, and benzoic acid.

2. The composition of claim 1, consisting of about 0.02-20% glycerin, about 0.1-30% propylene glycol, about 3-15% stearyl alcohol, about 0.1-15% cetyl alcohol, about 0.1-5% polysorbate 20, about 0.01-3% isopropyl myristate, about 0.01-5% C12-15 alkyl benzoate, about 0.01-1% benzoic acid, and water, wherein the pH of said composition being between about 4 to about 8.

3. The composition of claim 2, consisting of the following % (wt/wt) components:
Water 64.90
Propylene Glycol 0.20
Glycerin 20.00
Stearyl Alcohol 8.50
Cetyl Alcohol 3.00
Polysorbate 20 2.00
Isopropyl Myristate 1.00
C12-15 Alkyl Benzoate 0.20 and
Benzoic Acid 0.20,
wherein said composition has a pH of about 6.

4. A method of producing the non-tumorigenic skin care composition of claim 1 comprising the steps of
   a) mixing water, propylene glycol and glycerin and heating the resulting mixture to 75-80° C. with stirring;
   b) mixing polysorbate 20, cetyl alcohol, stearyl alcohol, isopropyl myristate, C12-15 alkyl benzoate and benzoic acid and heating the resulting mixture to about 75° C. with stirring;
   c) mixing the contents of a) and b) with stirring for a suitable time period at about 75° C.;
   d) cooling down the mixture of c) to approximately 30° C.; and
   e) adjusting the pH of the mixture of c) to approximately 5.9 with NaOH, thereby producing a non-tumorigenic skin care composition.

* * * * *